United States Patent
Levitan (10) Patent No.: US 11,690,967 B2
(45) Date of Patent: Jul. 4, 2023

(54) INTRODUCER FOR TRACHEAL TUBE INTUBATION

(71) Applicant: Richard M. Levitan, Orford, NH (US)

(72) Inventor: Richard M. Levitan, Orford, NH (US)

(*) Notice: Subject to any disclaimer, the term of this patent is extended or adjusted under 35 U.S.C. 154(b) by 652 days.

(21) Appl. No.: 16/741,946

(22) Filed: Jan. 14, 2020

(65) Prior Publication Data

US 2020/0164167 A1    May 28, 2020

Related U.S. Application Data

(63) Continuation of application No. 15/511,654, filed as application No. PCT/US2015/050452 on Sep. 16, 2015, now Pat. No. 10,569,039.

(60) Provisional application No. 62/054,487, filed on Sep. 24, 2014, provisional application No. 62/051,464, filed on Sep. 17, 2014.

(51) Int. Cl.
*A61M 16/04* (2006.01)
*A61B 1/267* (2006.01)

(52) U.S. Cl.
CPC ......... *A61M 16/0488* (2013.01); *A61B 1/267* (2013.01); *A61M 16/0484* (2014.02)

(58) Field of Classification Search
CPC .... A61M 16/04; A61M 16/0488; A61B 1/267
See application file for complete search history.

(56) References Cited

U.S. PATENT DOCUMENTS

| 3,957,055 A | 5/1976 | Linder et al. |
| 4,448,741 A | 5/1984 | Schad |
| 5,259,377 A | 11/1993 | Schroeder |
| 5,529,738 A | 6/1996 | Mercereau |

(Continued)

FOREIGN PATENT DOCUMENTS

| EP | 0465942 A1 | 1/1992 |
| EP | 1786362 A1 | 5/2007 |

(Continued)

OTHER PUBLICATIONS

Non-Final Rejection for U.S. Appl. No. 16/075,226; dated Apr. 14, 2020 (11 pages).

(Continued)

*Primary Examiner* — Christopher J Beccia
(74) *Attorney, Agent, or Firm* — Mendelsohn Dunleavy, P.C.; Eri Yoneda (57) ABSTRACT

An introducer for tracheal tube intubation has a proximal section connected to a distal section having an angled bougie tip. The introducer is configurable (i) for use as a bougie in which a tracheal tube is railroaded over the introducer's back end and into a trachea and (ii) for use as a stylet in which a tracheal tube is pre-loaded onto the introducer for insertion into a trachea. In certain embodiments, the introducer has one or more flexible or malleable sections that enable the introducer to bend into different configurations. The flexible/malleable sections have directional bending such that the sections bend in roughly the same plane as the angled bougie tip. This enables an operator always to know the orientation of the bougie tip even after it has been inserted into the trachea. The flexible/malleable sections enable the introducer to be configured with a handle or other type of grip.

16 Claims, 7 Drawing Sheets

(56) References Cited

U.S. PATENT DOCUMENTS

| | | |
|---|---|---|
| 5,761,759 A | 6/1998 | Leversby et al. |
| 5,769,506 A | 6/1998 | Boucherie |
| 6,579,485 B2 | 6/2003 | Smith et al. |
| 6,972,106 B2 | 12/2005 | Huber et al. |
| 7,083,756 B2 | 8/2006 | Strahler |
| 7,108,815 B2 | 9/2006 | Lee |
| 7,650,886 B1 | 1/2010 | Keller et al. |
| 7,655,543 B2 | 2/2010 | Bauer |
| 8,066,926 B2 | 11/2011 | Fogarty |
| 8,435,433 B2 | 5/2013 | Pennell et al. |
| 9,844,899 B2 | 12/2017 | Gauthier et al. |
| 10,105,886 B2 | 10/2018 | Maslakow et al. |
| 10,569,039 B2 * | 2/2020 | Levitan .......... A61B 1/267 |
| 2002/0074688 A1 | 6/2002 | Smith et al. |
| 2002/0171169 A1 | 11/2002 | Chuang |
| 2005/0244611 A1 | 11/2005 | Deininger et al. |
| 2006/0110704 A1 | 5/2006 | Bills |
| 2007/0287961 A1 | 12/2007 | Parker |
| 2007/0290399 A1 | 12/2007 | Easter et al. |
| 2008/0017195 A1 | 1/2008 | Yoshida |
| 2008/0087795 A1 | 4/2008 | Smith |
| 2009/0161063 A1 | 6/2009 | Parent |
| 2010/0108060 A1 * | 5/2010 | Pecherer .......... A61M 16/0488 128/200.26 |
| 2010/0152678 A1 | 6/2010 | Jakob |
| 2011/0120458 A1 | 5/2011 | Schwartz et al. |
| 2011/0265789 A1 | 11/2011 | Gabriel |
| 2012/0204867 A1 | 8/2012 | Levitan |
| 2012/0298102 A1 | 11/2012 | Levitan |
| 2013/0035548 A1 | 2/2013 | Ianchulev |
| 2013/0096482 A1 | 4/2013 | Bertrand et al. |
| 2013/0211263 A1 | 8/2013 | Boedeker |
| 2013/0245372 A1 | 9/2013 | Lo |
| 2014/0165799 A1 | 6/2014 | Gauthier et al. |
| 2014/0238390 A1 | 8/2014 | Wei et al. |
| 2015/0018915 A1 | 1/2015 | Leven |
| 2015/0021817 A1 | 1/2015 | Romero et al. |
| 2015/0042011 A1 | 2/2015 | Huang |
| 2015/0080989 A1 | 3/2015 | Mohn et al. |
| 2015/0290414 A1 | 10/2015 | Vasan |

FOREIGN PATENT DOCUMENTS

| | | | |
|---|---|---|---|
| EP | 1786362 | B1 | 4/2015 |
| GB | 2017504 | B | 9/1982 |
| GB | 2507474 | A | 5/2014 |
| JP | 01174426 | A | 7/1989 |
| JP | 06170889 | A | 6/1994 |
| WO | 9310840 | A1 | 6/1993 |
| WO | 2006017667 | A1 | 2/2006 |
| WO | 2007093786 | A1 | 8/2007 |
| WO | 2013059324 | A1 | 4/2013 |
| WO | 2015157657 | A1 | 10/2015 |

OTHER PUBLICATIONS

First Office Action for Chinese application No. 201680064845.4; dated Aug. 25, 2019; Machine Translation (15 pages).
International Search Report and Written Opinion; dated Jan. 28, 2016 for the corresponding International Patent Application No. PCT/US2015/050452.
Chinese Office Action dated Feb. 15, 2019 for the corresponding Chinese Patent Application No. 201580062191.7.
European Office Action dated Apr. 9, 2019 for the corresponding European Patent Application No. 15 771 407.2.
EUIPO Design Registration No. 002600932-0001; Registered on Dec. 18, 2014; Owner: VBM Medizintechnik GmbH.
Extended European Search Report for corresponding European application No. 20209455.3; dated Mar. 9, 2021 (7 pages).
Final Office Action for U.S. Appl. No. 15/773,923; dated Mar. 1, 2021 (10 pages).
Second Office Action for Chinese application No. 201680064845.4; dated Jun. 30, 2020; 16 pages (Machine Translation).
Communication pursuant to Article 94(3) EPC for European application No. 16797483.1; dated Jun. 3, 2020; (4 pages).
Non-Final Office Action for U.S. application No. 15/773,923; dated Aug. 20, 2020 (10 pages).
First Office Action for Chinese application No. 201780009914.6; dated Jul. 3, 2020, 20 pages (Machine Translation).
Final Rejection for U.S. Appl. No. 16/075,226; dated Aug. 27, 2020 (14 pages).
Communication pursuant to Article 94(3) EPC for European application No. 16797483.1; dated Apr. 9, 2021 (4 pages).

* cited by examiner

INTRODUCER FOR TRACHEAL TUBE INTUBATION

CROSS-REFERENCE TO RELATED APPLICATIONS

This application is a continuation of U.S. patent application Ser. No. 15/511,654, filed on Mar. 16, 2017, which claims the benefit of the filing dates of U.S. provisional application No. 62/051,464, filed on Sep. 17, 2014, and 62/054,487, filed on Sep. 24, 2014, the teachings of all of which are incorporated herein by reference in their entirety.

BACKGROUND

Field of the Invention

The present invention relates to medical devices and techniques for using medical devices and, more specifically but not exclusively, to introducers for tracheal tube insertion (intubation) using direct laryngoscopes and video laryngoscopes.

Description of the Related Art

This section introduces aspects that may help facilitate a better understanding of the invention. Accordingly, the statements of this section are to be read in this light and are not to be understood as admissions about what is prior art or what is not prior art.

Emergency intubation is accomplished through direct or video imaging of the larynx, followed by tracheal tube insertion under vision, i.e., the tube is manipulated by the operator and seen entering the larynx. Since the distal end of a tracheal tube may block direct visualization of the larynx during the insertion process, a variety of techniques have been devised to overcome this visualization challenge. In 1949, Macintosh suggested the use of a gum-elastic catheter, now commonly called a bougie, to aid in tube insertion. The bougie is a rounded tube introducer, approximately 15Fr (i.e., 5 mm) diameter and about 70 centimeters in length, with a Coude tip that is angled slightly upward (approximately 38 degrees in the original Portex device manufactured by Smiths Medical International Ltd of Kent, United Kingdom). Throughout much of Europe and the United Kingdom, this device is considered an essential piece of equipment when inserting tubes using direct laryngoscopy.

Patient outcomes in emergency airway management show a strong correlation between adverse events and number of intubation attempts. Many operators and emergency systems advocate the use of a bougie on all initial attempts should intubation be required.

In the U.S., malleable stylets were developed for controlling the insertion of tracheal tubes. Levitan et al. has described the optimal technique for shaping a stylet as "straight-to-cuff," to denote where the bend point of a styletted tube should be. See Levitan R M, Pisaturo J T, Kinkle W C, Butler K, Everett W W, "Stylet bend angles and tracheal tube passage using a straight-to-cuff shape," *Acad Emerg Med* 2006, 13:1255-8. Levitan et al. advocate a 35-degree bend. In their opinion, this maximizes visualization, facilitates insertion, and minimizes the impaction of the tracheal tube tip on the tracheal rings.

The anterior two thirds of the trachea has cartilaginous rings that help preserve the patency of the airway. When inserting the bougie, which is flexible, and has an upturned tip, the tip will interact with the rings, creating a palpable click that is felt in 65-95% of insertions into the trachea. If the tip of the bougie is inserted into the esophagus, then these rings are not felt. The tactile feedback of being in the trachea is not perfect, however, because of several variables. If the tip rotates so that it is not directed anteriorly, then it will slide along the membranous trachea, which has no rings.

In situations of difficult laryngoscopy, the bougie may be blindly placed under the epiglottis, and, through tactile feedback, verification of tracheal insertion is provided, even when direct visualization of the glottis opening is limited. The bougie is very long (~60-70 cm), and unfortunately it may be difficult to effectively control the distal tip, making sure that the distal tip stays upright, hugging the undersurface of the epiglottis on insertion. It is very susceptible to unrecognized rotation because of its uniformly round shape. It has no inherent directionality, apart from the distal tip, which becomes invisible after insertion. Finally, using the bougie is a two-person task. The operator places the device (while continuing to hold a laryngoscope), while an assistant helps railroad the tube. The tube cannot be preloaded on a bougie and held initially by the operator, because the tube will slide over the bougie, i.e., the two devices do not move as a unit.

Stylets have the advantage of being faster because they are inserted along with the tracheal tube. If shaped improperly, however, they can make intubation more difficult, either by blocking the line of sight, or through catching on the anterior tracheal rings. Stylet bend angles above 35 degrees, for instance, commonly cause tracheal ring impaction when using standard tubes with asymmetric left-facing bevels. See Levitan et al.

Styletted tubes do not provide tracheal-ring tactile feel, and, if the stylet is inadvertently allowed to project beyond the tube, then it can cause tracheal perforation. Even if the end of the stylet stops within the tracheal tube tip, if the stylet is too close to the tube tip, then it will stiffen the tip too much causing it to impact on the trachea. The trachea has a dimension of about 14-16 mm in female adults and about 16-20 mm in male adults. An excessive bend easily causes the tip to engage the tracheal rings. This may prevent tube insertion mechanically or result in tracheal trauma that could result in tears and other injuries. When tracheal tube advancement problems occur, the operator may need to rotate the tube (changing the bevel orientation) or stabilize the tube and remove the stylet before attempting re-insertion. In emergency situations, such delays may be consequential, and, if the intubation attempts are repeated multiple times, then there are high rates of adverse events.

Recently, hyper-angulated rigid stylets have been developed to use with hyper-angulated video laryngoscopes. Video laryngoscopes, like the Glidescope video laryngoscope from Verathon, Inc., of Bothell, Wash., use a curved tongue retractor and a video camera to image the larynx. These devices are hyper-angulated relative to the shape of a standard Macintosh curved laryngoscope blade. In order to deliver a tube to the larynx, however, a tube must follow the hyper-angulated blade around the tongue and be inserted into the trachea. Once the tip is in the trachea, the tube has to take a more-posterior angle to enter the trachea. The trachea follows the thoracic spine, i.e., it dives posteriorly. This creates a fundamental tube-delivery challenge with any hyper-angulated video laryngoscope. A stiff hyper-angulated tube—needed for rotation around the tongue—is too stiff for insertion into the trachea. It also has a side-to-side, long-axis dimension that exceeds the diameter of the trachea. See Levitan R M, Heitz J W, Sweeney M, Cooper R M, "The Complexities of Tracheal Intubation With Direct Laryngoscopy and Alternative Intubation Devices," *Ann Emerg Med* 2011; 57:240-7. Numerous case reports have documented the hazards of hyper-angulated rigid stylets using video laryngoscopes.

BRIEF DESCRIPTION OF THE DRAWINGS

Other embodiments of the invention will become more fully apparent from the following detailed description, the appended claims, and the accompanying drawings in which like reference numerals identify similar or identical elements.

DETAILED DESCRIPTION

In certain embodiments of this disclosure, an improved introducer for tracheal tube intubation works with both direct laryngoscopes and video laryngoscopes. It improves on the design of a stylet by having a rounded distal tip, eliminating the risk of trachea injury. Nonetheless, it still has enough rigidity to allow for shaping of an overlying tube for either direct or video laryngoscopy. Like stylets, it has a proximal end with a mechanism for fast removal of the stylet from the tracheal tube (after the tube has been placed in the trachea).

The improved introducer also functions effectively as a bougie, permitting tactile feel of the trachea, and allowing railroading of a tracheal tube over the back end of the device and into the trachea. Unlike conventional rounded bougies, it also has inherent directionality, thereby enabling the operator always to know the direction of the upturned distal tip (even when not visible—as often occurs with conventional bougies as the tip is passed under the epiglottis).

Inserting tubes into the trachea using stylets (in order to create a straight-to-cuff shape and a narrow long axis) can be problematic if the stylets' rigidity prevents their insertion. Although a low bend angle (<35 degrees) reduces this risk, it does not eliminate it. As already mentioned, the shape of the tracheal tube tip, especially when a rigid stylet is placed to the end of the tube, can impact on the tracheal rings. If the stylet projects beyond the tube tip, it is especially dangerous due to its rigidity and small diameter. Although bougies have a lower risk of catching on the trachea rings, the commonly used, single-use plastic varieties of bougies can be quite rigid down their long axis and can also cause tracheal injury (perforation), or the tip can catch on the tracheal rings.

Like a stylet, the improved introducer permits shaping with the tube loaded on for visualization during placement (either (i) a low-axis, ~35-degree bend for direct laryngoscopy or (ii) a more-exaggerated, ~70-degree bend for hyper-angulated blades used with a Glidescope video laryngoscope), but, at the same time, allows "un-bending" on insertion after the tube tip has passed into the trachea. Like a bougie, the improved introducer is rigid enough to maintain its narrow, long axis on insertion to the larynx, but is also not too rigid (in order to "un-bend") as it passes the vocal cords and moves down the trachea.

The improved introducer permits one-handed placement of bougie and tube. The improved introducer has the short storage length and easy handling of a stylet, but the functional length and performance of a bougie when needed. Since the improved introducer functions equally well as a bougie or a stylet, it allows a reduction from two devices to only one needed device. Saving space and reducing complexity (stocking requirements) are important in many settings where emergency airways are needed, i.e., emergency services, tactical situations, ambulances, helicopters, etc. The improved introducer also allows one-handed conversion from use of the device as a stylet to use as a bougie, which is advantageous when unexpected tube insertion difficulty is encountered.

Figure 1A:
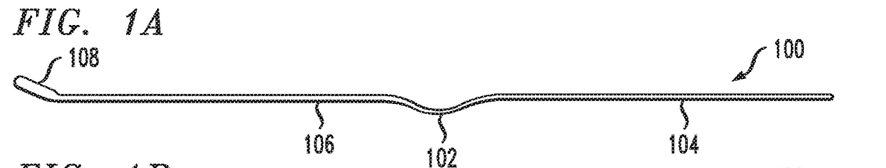
FIG. 1A is a side view of an introducer according to a first embodiment of this disclosure.
Figure 1B:
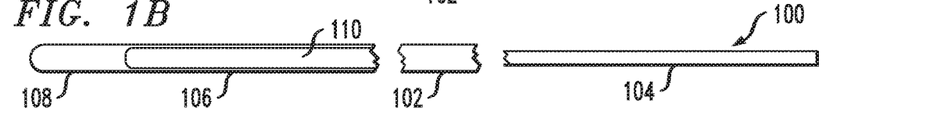
FIG. 1B is a broken top view of the introducer of FIG. 1A.
Figure 1C:
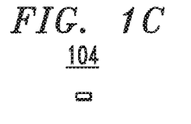
FIG. 1C is a cross-sectional end view of section 104 of the introducer of FIGS. 1A and 1B.
Figure 1D:
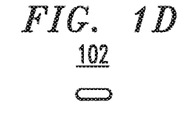
FIG. 1D is a cross-sectional end view of section 102 of the introducer of FIGS. 1A and 1B.
Figure 1E:
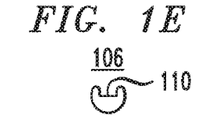
FIG. 1E is a cross-sectional end view of section 106 of the introducer of FIGS. 1A and 1B.
Figure 1F:
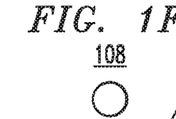
FIG. 1F is a cross-sectional end view of section 108 of the introducer of FIGS. 1A and 1B.

FIGS. 1A-1K show an improved introducer 100 according to certain embodiments of the disclosure. FIG. 1A shows a side view of introducer 100 in its fully open, straight configuration (e.g., for use as a bougie), while FIG. 1B shows a top, plan view of portions of different sections of introducer 100. As shown in FIGS. 1A and 1B, introducer 100 has a hinge 102 connecting a proximal "stylet" section 104 to a distal "bougie" section 106. In one embodiment, the proximal stylet section 104 is made from a malleable metal rod, hinge 102 is made from a malleable plastic, and the distal bougie section 106 has the mechanical properties, tip 108, and bend shape of a standard plastic bougie. The tip 108 is rounded similar to the shape of a bougie tip for interacting with the tracheal rings. The hinge section allows the introducer to bend over on itself. As described below, the proximal stylet section 104 is relatively thin and can fit within a recess 110 in the top half of the wider, distal bougie section 106.

FIGS. 1C-1F show lateral cross-sectional views of different sections of introducer 100, where the proximal stylet section 104 and hinge 102 each have a generally rectangular lateral cross section, with the hinge defined by a larger of the two rectangles. The distal bougie section 106 and the tip 108 have generally circular lateral cross sections of substantially equal diameter, except that the distal bougie section 106 has a longitudinal recess 110 that is sized and shaped to receive the proximal stylet section 104, for example, with a friction fit, when the introducer 100 is folded upon itself at hinge 102 (as shown, for example, in FIGS. 1I-1K). In alternative designs, the longitudinal recess 110 is omitted and/or the proximal stylet section is cylindrical, similar to the rounded wire used in a standard steel stylet. The wire used for the proximal section 104 should be stiff enough to hold the shape of an overlying tube, and small enough to fit alongside the distal bougie section 106 without exceeding an outer diameter of ~5 mm (so that it will slide easily within adult tracheal tubes having 6.5-8.5 mm inner diameters).

There are numerous manners in which the hinge section 102 could be constructed. In the embodiment shown in FIGS. 1A, 1B, and 1D, the hinge's rectangular cross section allows the hinge to bend up and down, but has inherent relative side-to-side strength. The hinge section could be modified with ridges, or other modifications to facilitate the bending needed, but also allow creation of a loop for removal of the introducer when it is used a stylet. The hinge 102 should be strong enough to keep proximal stylet section 104 and the distal bougie section 106 moving in the same plane (bending up and down, but not side-to-side). It should also permit straightening, so that, when the introducer is used as a bougie, a tube can be slid down the proximal end, over the hinge, and into the trachea.

Figure 1G:
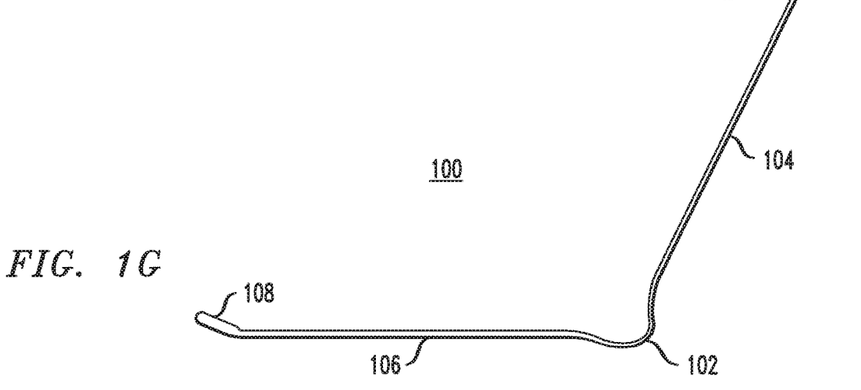
FIG. 1G shows the introducer of FIGS. 1A and 1B configured for use as a bougie.

FIG. 1G shows introducer 100 configured for use as a bougie with hinge 102 bent to form an angle of about 100 degrees between the proximal stylet section 104 and the distal bougie section 106. Because of the flattened shape of the hinge section 102, the proximal stylet section 104 can be configured to be roughly perpendicular to and approximately co-planar with the upturned tip 108 of the distal bougie section 106. When introducer 100 is used as a bougie for intubation, the operator knows the direction of the distal tip 108 because of the directionality provided to the introducer by the geometric relationship established between the bougie tip and the proximal section by the hinge 102. Just like a bougie, after placement of the introducer within the trachea, a tracheal tube can be advanced over the back end of the introducer and railroaded into the trachea.

Figure 1H:
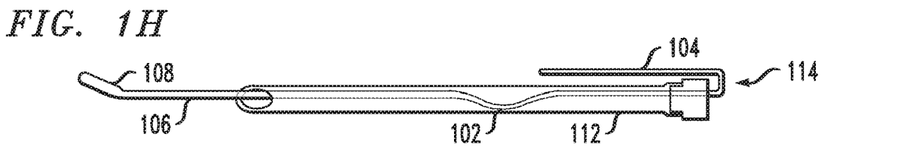
FIG. 1H shows the introducer of FIGS. 1A and 1B preloaded with a tracheal tube.

FIG. 1H shows introducer 100 preloaded with a tracheal tube 112 with the proximal stylet section 104 folded over the proximal end of the tube to prevent the tube from sliding off the proximal end of the introducer and to form a handle 114 that provides directionality to introducer 100. Unlike a standard bougie, in this configuration, introducer 100 can be preloaded with a tracheal tube and used with a one-hand technique. When the introducer and tube are held together, the devices do not slide on one another.

Figure 1I:
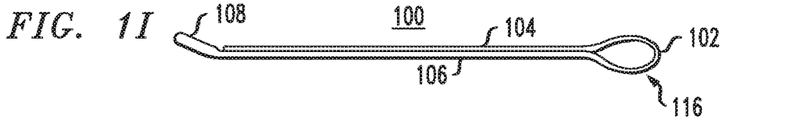
FIG. 1I shows the introducer of FIGS. 1A and 1B configured for efficient storage.

FIG. 1I shows introducer 100 configured for efficient storage or for stylet use with the proximal stylet section 104 folded onto the distal bougie section 106 where the bent hinge 102 forms a handle 116 that provides directionality to introducer 100. With the introducer folded on itself, it has the rigidity to shape a tracheal tube, and can be bent into a shape needed for direct laryngoscopy or video laryngoscopy. Note that, when introducer 100 is folded into this stylet-use configuration, the bougie tip 108 extends beyond the proximal stylet section 104. This prevents the rigid stylet section from injuring the trachea if the tip of the introducer extends beyond the length of the tube. Although not depicted in FIG. 1I, introducer 100 can be configured such that the proximal stylet section 104 fits at least partially if not completely within recess 110 of the distal bougie section 106 to provide the introducer with a very low profile.

Figure 1J:
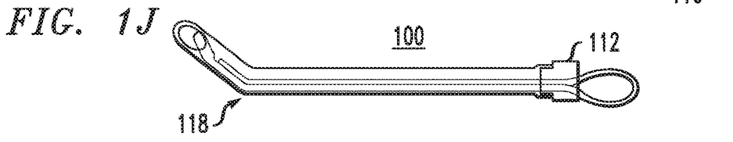
FIG. 1J shows the introducer of FIGS. 1A and 1B configured as in FIG. 1I and pre-loaded with a tracheal tube for direct laryngoscopy.
Figure 1K:
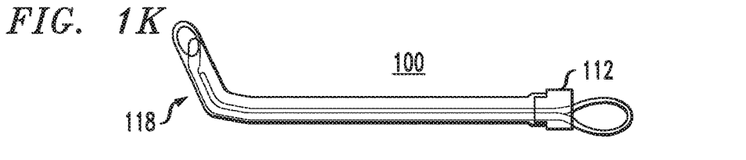
FIG. 1K shows the introducer of FIGS. 1A and 1B configured as in FIG. 1I and pre-loaded with a tracheal tube for video laryngoscopy.

FIGS. 1J and 1K show introducer 100 configured as in FIG. 1I and pre-loaded with tracheal tube 112 for use as a stylet for direct and video laryngoscopy, respectively, where the distal end 118 of the folded-over sections 104 and 106 is bent approximately 35 degrees for direct laryngoscopy (FIG. 1J) and approximately 70 degrees for video laryngoscopy (FIG. 1K). In these configurations, the handle 116 formed by the hinge 102 functions as a grab loop for removal of the introducer after the tube tip has been placed into the trachea.

Introducer 100 may have a lubricious coating to permit removal of the introducer through a tracheal tube either when used as a bougie or when doubled over on itself and used as a stylet.

Figure 2A:
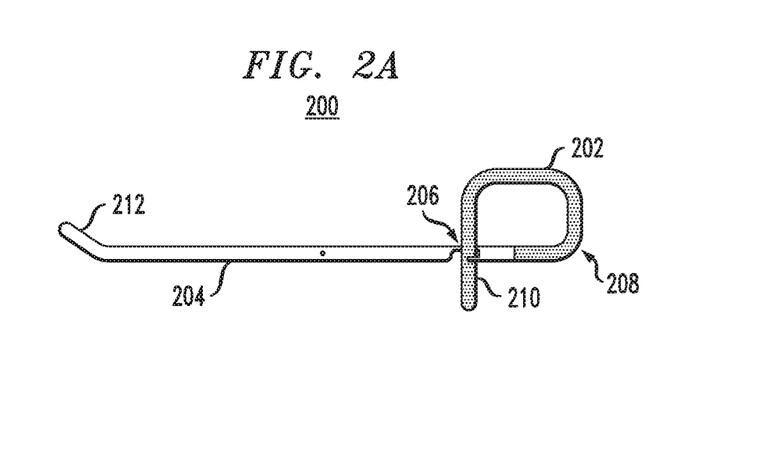
FIG. 2A is a side view of an introducer according to a second embodiment of this disclosure configured for use as a stylet or as a bougie.
Figure 2B:
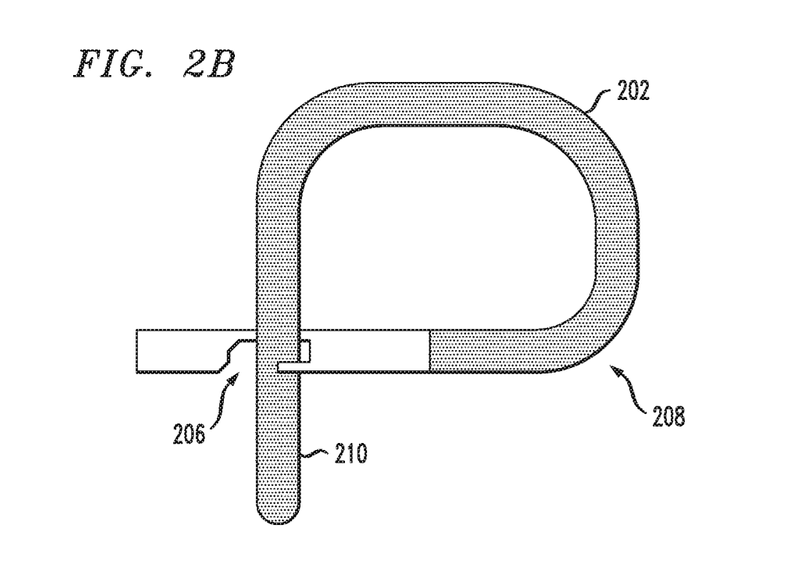
FIG. 2B shows a close-up, side view of the handle of the introducer of FIG. 2A.

FIGS. 2A-2B shows an improved introducer 200 according to certain other embodiments of the disclosure. FIG. 2A shows a side view of introducer 200 configured for use as a stylet or as a bougie, depending on whether or not a tracheal tube (not shown) is pre-loaded onto the introducer. Introducer 200 has a malleable proximal section 202 connected to a distal main body 204 by an attachment mechanism 206. In the configuration shown in FIG. 2A, the proximal section 202 has been bent by about 90 degrees at three different locations to form a handle 208, where the back end 210 of proximal section 202 engages with the attachment mechanism 206 to secure the proximal section in place and retain its handle-forming shape.

FIG. 2B shows a close-up, side view of the handle 208 of FIG. 2A formed by the bent proximal section 202 and attachment mechanism 206.

In this embodiment, introducer 200 is a rod of a length between 50 and 65 cm. When the proximal section 202 does not engage the attachment mechanism 206, this length enables introducer 200 to be used as a bougie, where the introducer tip 212 is inserted into the trachea (it is approximately 16 centimeters from the teeth to the laryngeal entrance), and a tracheal tube (not shown) of approximately 30-34 cm is subsequently inserted over (i.e., railroaded down) the back end 210 of the introducer and into the trachea. Note that attachment mechanism 206 is designed such that, after the bougie tip 212 of the introducer configured as shown in FIG. 2A has been inserted into the trachea, the operator can disengage the attachment mechanism (e.g., with the same hand that is holding the introducer) to allow the proximal section 202 to unfold and a tracheal tube to be railroaded down the introducer's back end 210 and into the trachea (e.g., using the operator's free hand).

The distal tip 212 of introducer 200 is upturned at an angle of approximately 35 degrees (between 30 and 40 degrees) to be similar in shape and mechanical flexibility as the tips of conventional bougies. The upturned tip 212 preferably does not exceed 30 millimeters in length, and the total length of the upturned tip 212 and the main body 204 does not exceed about 25 millimeters. The average trachea has an anterior-posterior dimension of 14-16 mm in women and 15-20 millimeters in men. If the total length of the upturned tip and the main body is too large, then introducer 200 might not be able to be inserted into the trachea without catching on the anterior tracheal rings.

In some implementations, the bending of introducer 200 has directionality resulting from the presence of a flat malleable wire (not shown) embedded in the rod, beginning at a point behind the upturned distal tip 212 and extending proximally approximately 30 centimeters towards the back end 210. The flat malleable wire (a metal or a plastic that can retain its shape) provides the rigidity for holding a tracheal tube in a predetermined shape. Tracheal tubes have an inherent arcuate shape, and a standard bougie cannot keep such tubes in a straightened position. Conversely, this is exactly what a stylet does—allowing straightening of the main body of the tube (and upturning the distal tip). The flatness of the malleable wire means that the introducer will tend to bend such that the introducer retains its anterior-posterior orientation, i.e., bending will be preferentially up/down as opposed to what would occur with a round wire embedded within a round rod. One implementation employs an elliptical rod (wider in its side-to-side dimension than its top-to-bottom dimension) along its entire length. This shape would cause preferential bending along the entire rod as well as along the embedded wire section.

There is an added advantage to an elliptical rod shape. When sliding a tracheal tube down such an elliptical rod, there will be less of a gap on the sides of the rod (between the outer diameter of the rod and the inner diameter of an overlying tracheal tube) than there will be between the top and bottom of the rod and overlying tube. This lateral gap is significant because, if too great a disparity exists, then the tube can catch on the laryngeal inlet as it is railroaded over the introducer. Almost all tracheal tubes use a left-facing bevel design in which the tip is not symmetric, where the main bevel faces −90 degrees from vertical when viewing a tube down its long axis, and a Murphy eye (an elliptical hole in the body of the tube within an inch of the distal tip) is located on the opposite right (+90 degree) position. The leading edge of left-facing beveled tubes is therefore located at +90 degrees. Standard tubes have a left-facing bevel, either with a straight cut, or a slight rounded tip. A Parker tube has a symmetric ski-tip shaped tip. Turning tracheal tubes to the right when they contact the tracheal rings causes the bevel to face upwards, and the inclination to turn down, facilitating insertion. When a gap exists between a bougie (typically sized at 5 millimeters outer diameter) and an overlying tube (anywhere from 7.0-9.0 millimeters internal diameter in adults), the gap hits the right arytenoid and aryepiglottic fold. The elliptical rod for introducer 200 could be slightly larger than a standard bougie in its side-to-side dimension, and conversely smaller in its top-to-bottom dimension, which would minimize the lateral gap, but still have a similar amount or less surface contact between devices (which would inhibit the tube from sliding over the bougie).

Located between about 30 cm and about 50 cm from the distal tip 212, the attachment mechanism 206 allows the bent proximal section 202 to be locked into a fixed position approximately perpendicular to the main body 204, as shown in FIG. 2A. This bending of the proximal section 202 over the main body 204 creates a T-shape (i.e., between the main body 204 and the straight back end 210 of the proximal section 202), with the back end 210 extending a distance (below the axis of the main body 204) preferably not to exceed 50 millimeters. The resulting handle 208 is in alignment (i.e., roughly co-planar) with the orientation of the distal upturned tip 212 of the introducer. This relative orientation results from the flat wire, the way the attachment mechanism 206 engages the back end 210, and/or the elliptical shape of the rod.

FIG. 2B shows attachment mechanism 206 corresponding to one possible design for engaging with the back end 210 of the bent proximal section 202. A variety of other designs are possible. These include, without limitation, a pin or hook connection, a locking-snap mechanism, or small magnetic clips. Some possible designs enable attachment (e.g., crossing of the sections) at any several points along the proximal section 202 from the back end 210 of the malleable wire to approximately 5 centimeters from the attachment mechanism 206. This would allow bending (and locking) the introducer on itself with either a large handle or a short handle, allowing the operator to vary the functional length of the introducer.

Introducer 200 can be configured for use as a standard bougie, e.g., fully extended (straight), such that a tube can be railroaded over its length and into the trachea.

By bending the proximal section 202 and securing it using the attachment mechanism 206), the introducer's effective length is shortened which makes it easier to handle and insert into the trachea. The resulting handle 208 provides an ergonomically effective way to control the introducer and also gives the operator an indication of the orientation of the upturned tip 212. Once the tip 212 has been inserted into the trachea, the attachment mechanism 206 can be easily released, e.g., by the operator's single hand holding the introducer at the T-shaped intersection. This allows subsequent railroading of a tracheal tube over the device (with the released introducer now having no impediments to sliding of a tracheal tube down its length) and into the trachea. Accordingly, the attachment mechanism 206 (or other attachment points (not shown) on the main body 204) should be sufficiently low profile and/or shape not to restrict sliding of a tracheal tube down the introducer.

Alternatively, introducer 200 can be used as a stylet (shaped for either direct or video laryngoscopy), where a tracheal tube is pre-loaded onto the distal end of the introducer 200 pre-configured with a handle, as shown in FIG. 2A, with the distal tip 212 projecting beyond the pre-loaded tube and where the engagement of the bent proximal section 202 with the attachment mechanism 206 form a stop that prevents the tracheal tube from sliding any further towards the proximal end of the introducer.

FIGS. 3A-3F show an improved introducer 300 according to certain other embodiments of the disclosure. Introducer 300 is similar to introducer 200 of FIG. 2, except that the attachment mechanism 306 for introducer 300 is different from the attachment mechanism 206 of introducer 200. In particular, attachment mechanism 306 is a metal clip that wraps around the intersecting sections of the introducer 300 to hold them in place. Note that the attachment mechanism 206 of FIG. 2 is located at a fixed position along introducer 200, while attachment mechanism 306 of FIG. 3 is movable such that it can be re-located to different positions along introducer 300.

Figure 3A:
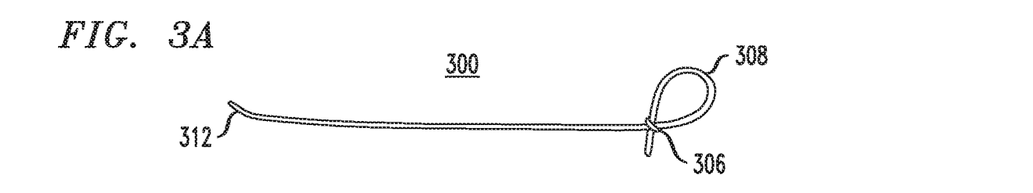
FIG. 3A is a side view of an introducer according to a third embodiment of this disclosure configured for use as a bougie with a relatively small handle.
Figure 3B:
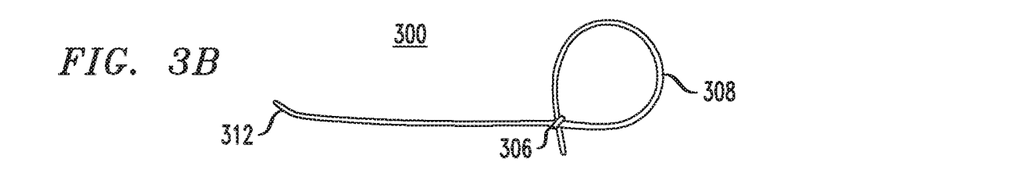
FIG. 3B is a side view of the introducer of FIG. 3A configured for use as a bougie with a relatively large handle.

FIG. 3A shows a side view of introducer 300 configured for use as a bougie with a relatively small handle 308, while FIG. 3B shows a side view of introducer 300 configured for use as a bougie with a relatively large handle 308. Note that the two different handle sizes are achieved by locating attachment mechanism 306 at two different positions along introducer 300.

Figure 3C:
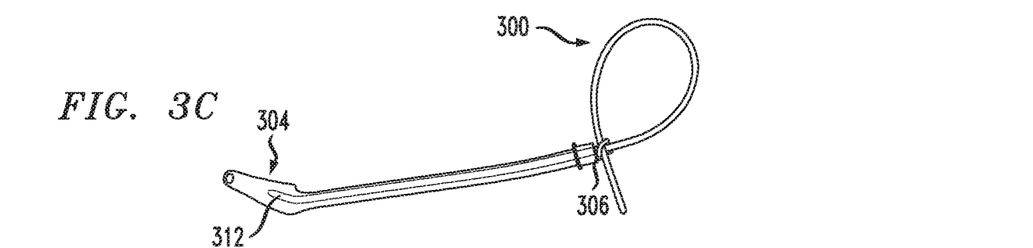
FIG. 3C is a side view of the introducer of FIG. 3A configured for use as a stylet for direct laryngoscopy.
Figure 3D:
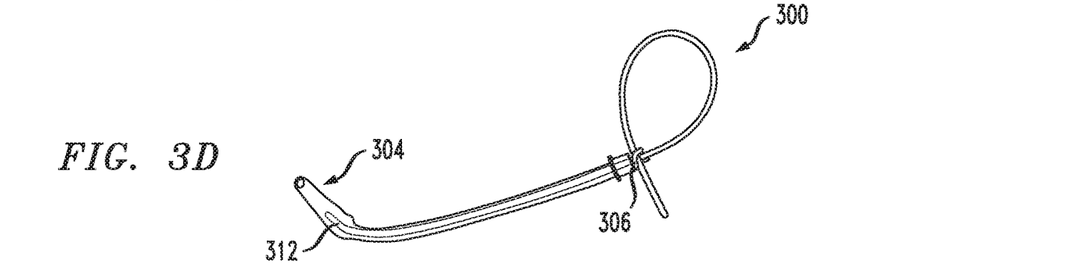
FIG. 3D is a side view of the introducer of FIG. 3A configured for use as a stylet for video laryngoscopy.

FIG. 3C shows a side view of introducer 300 configured for use as a stylet for direct laryngoscopy (i.e., about 35-degree bend at its distal end) with a pre-loaded tracheal tube 304, while FIG. 3D shows a side view of introducer 300 configured for use as a stylet for video laryngoscopy (i.e., about 70-degree bend at its distal end) with pre-loaded tracheal tube 304. Note that the location of attachment mechanism 306 in these two configurations results in the distal end of the tracheal tube extending beyond the distal tip 312 of introducer 300 in both FIGS. 3C and 3D.

Figure 3E:
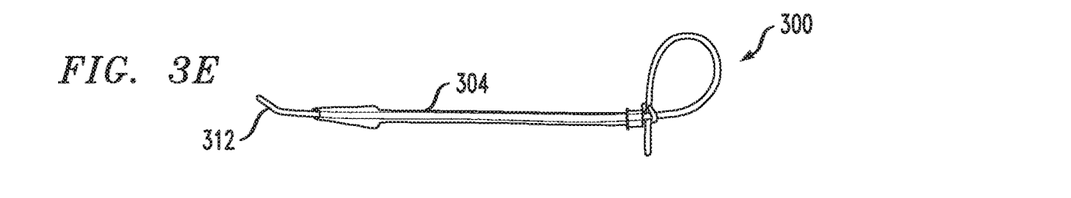
FIG. 3E is a side view of the introducer of FIG. 3A configured for use as a stylet for direct laryngoscopy with pre-loaded tracheal tube.
Figure 3F:
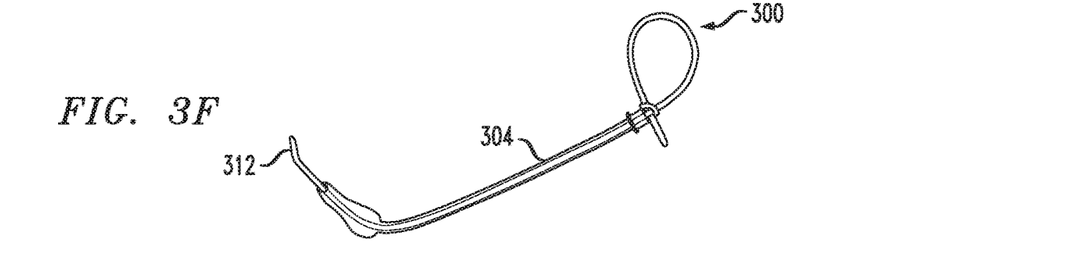
FIG. 3F is a side view of the introducer of FIG. 3A configured for use as a stylet for video laryngoscopy with pre-loaded tracheal tube.

FIGS. 3E and 3F respectively show side views of introducer 300 configured for use as a stylet for direct and video laryngoscopy with pre-loaded tracheal tube 304. Note that the location of attachment mechanism 306 in these two configurations results in the distal tip 312 of the introducer extending beyond the distal end of the tracheal tube and also in handle 308 in FIGS. 3E and 3F being smaller than handle 308 in FIGS. 3C and 3D. In all four configurations of FIGS. 3C-3F, the position of the attachment mechanism 306 determines the location of a stop that prevents further insertion of the tracheal tube 304 onto introducer 300.

FIGS. 4A-4E shows an improved introducer 400 according to certain other embodiments of the disclosure. Introducer 400 is similar to introducer 100 of FIG. 1, except that the attachment mechanism 406 for introducer 400 is different from the attachment mechanism 206 of introducer 200. In particular, attachment mechanism 406 consists of a fixed male component 402 and two fixed female components 404(1)-404(2) located at two different positions along introducer 400. In general, introducers may have one or more male components and one or more female components.

Figure 4A:
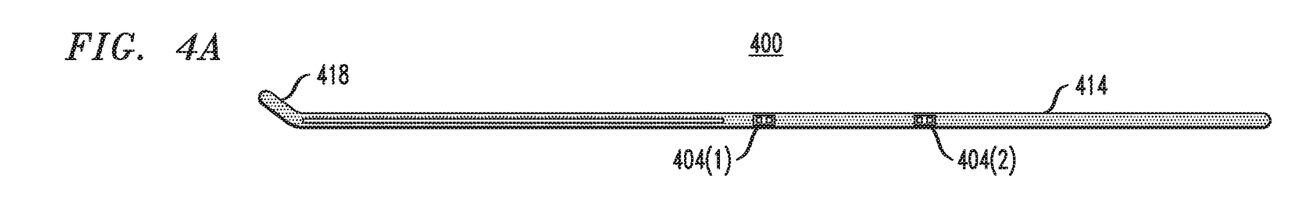
FIG. 4A is a side view of an introducer according to a fourth embodiment of this disclosure.
Figure 4B:
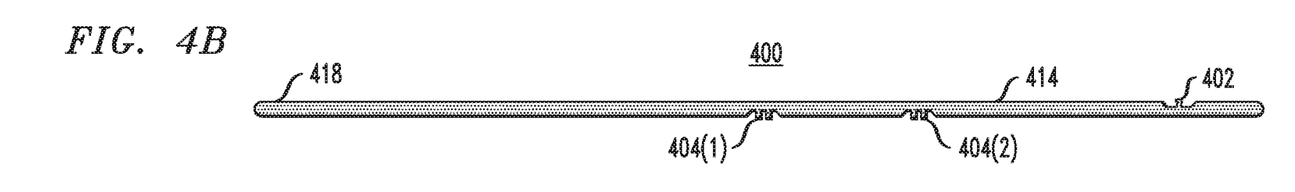
FIG. 4B is a top plan view of the introducer of FIG. 4A.

FIG. 4A shows a side view of introducer 400, while FIG. 4B shows a top plan view of introducer 400. Note that, since the male and female components are on opposite sides of the introducer, male component 402 is not visible in FIG. 4A.

Figure 4C:
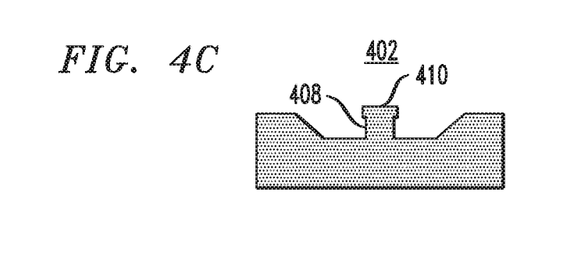
FIG. 4C is a close-up top view of the male component of the introducer of FIG. 4A.
Figure 4D:
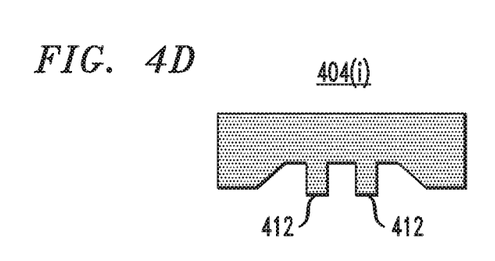
FIG. 4D is a close-up top view of one of the female components of the introducer of FIG. 4A.

FIGS. 4C and 4D respectively show close-up top views of male component 402 and female component 404(i). Male component 402 includes a cylindrical or rectilinear center post 408 capped by a cylindrical or rectilinear cap 410, whose width is larger than the width of the center post 408. Female component 404(1) includes two cylindrical or rectilinear posts 412 separated by a distance that is greater than the width of center post 408, but smaller than the width of cap 410. To engage the attachment mechanism 406, the proximal section 414 of introducer 400 is bent a total of about 270 degrees such that the center post 408 of male component 402 is located between the two posts 412 of female component 4040 with the cap 410 of male component 402 preventing the attachment mechanism 406 from dis-engaging and introducer 400 from unfolding.

Figure 4E:
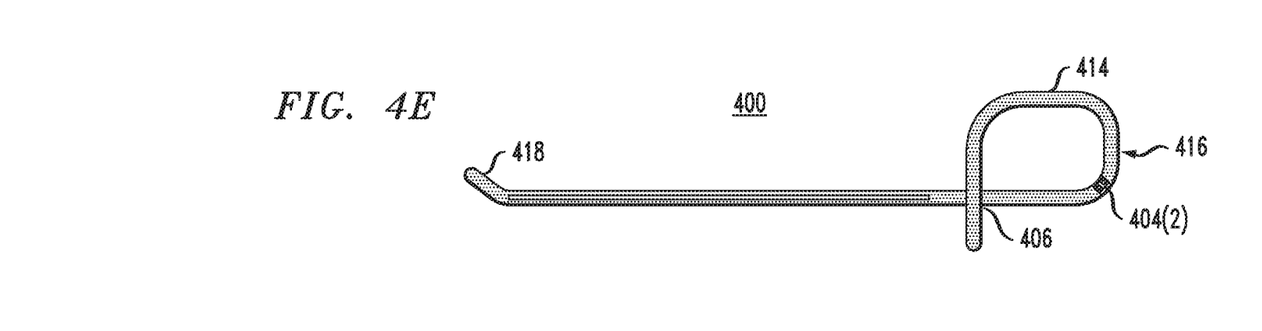
FIG. 4E shows the introducer of FIG. 4A configured with the male component engaging one of the female components to form a handle.

FIG. 4E shows introducer 400 configured with male component 402 engaging female components 4040 to form handle 416. Note that the positions of the two female components 404(1) and 404(2) along introducer 400 may be selected such that (i) configuring introducer 400 with male component 402 engaging female component 404(1) would result in a relatively large handle 416 for a stylet for which the distal end of a pre-loaded tracheal tube (not shown) would extend beyond the distal tip of the introducer, whereas (ii) alternatively configuring introducer 400 with male component 402 engaging female component 404(2) would result in a relatively small handle 416 for a stylet for which the distal tip of the introducer would extend beyond the distal end of the same-sized pre-loaded tracheal tube (not shown). Here, too, after insertion of the bougie tip 418 into the trachea, an operator can dis-engage the attachment mechanism 406 (for example, with one hand) to enable a tracheal tube to be railroaded over the introducer's back end and into the trachea (for example, using the operator's free hand).

Figure 5A:
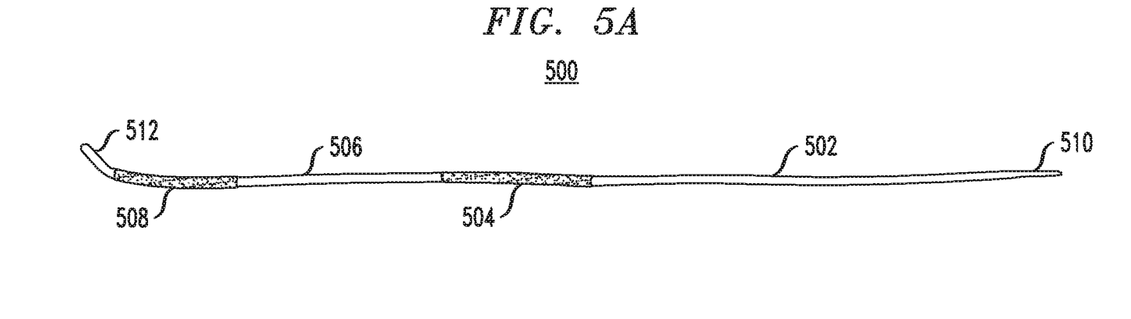
FIG. 5A is a side view of an introducer according to a fifth embodiment of this disclosure.
Figure 5B:
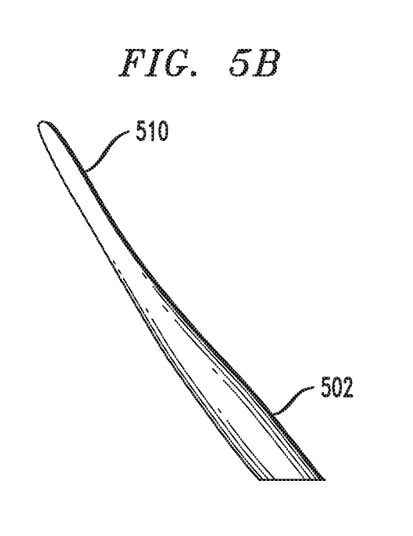
FIG. 5B is a close-up view of the proximal end of the introducer of FIG. 5A.
Figure 5C:
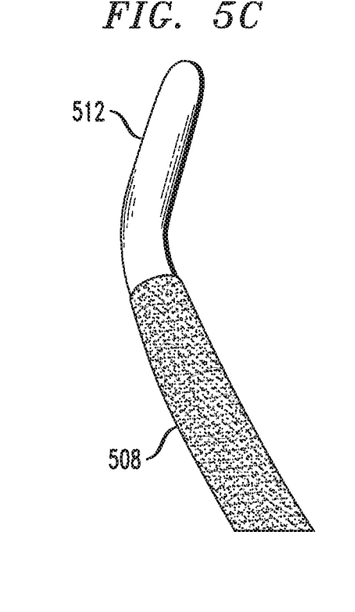
FIG. 5C is a close-up view of the distal end of the introducer of FIG. 5A.

FIGS. 5A-5I shows an improved introducer 500 according to certain other embodiments of the disclosure. FIG. 5A shows a side view of introducer 500. As shown in FIG. 5A, introducer 500 has a relatively flexible proximal section 502 connected to a first (proximal) malleable section 504 connected to a relatively flexible distal section 506 connected to a second (distal) malleable section 508. As shown in FIG. 5B, the proximal end of proximal section 502 has a flattened (or otherwise reduced-size) tip 510, while the distal end of the second malleable section 508 has a conventional bougie tip 512 as shown in FIG. 5C.

As used herein, the term "flexible" means that the section can be relatively easily bent, but does not necessarily retain its bent shape on its own and may require application of some external retaining force to keep the section in its bent shape. On the other hand, the term "malleable" means that the section can be bent and will retain its bent shape on its own without having to apply any external retaining force.

In one embodiment, introducer 500 has a total length between about 50 cm and about 70 cm. This length is for use as a bougie when the introducer tip 512 has been inserted into the trachea and a tracheal tube of approximately 30-34 cm is subsequently inserted (i.e., railroaded down) over the back end of the introducer and into the trachea.

Introducer 500 has directionality created by the presence of the two malleable sections 504 and 508. The second malleable section 508 begins at a point behind the upturned distal tip 512 and extends proximally approximately 15 centimeters. The first malleable section 504 is located between about 25 and about 45 centimeters from the distal tip 512. The malleable sections may be created by a tubular metallic material (including a hollow thin metallic rod, slid over the bougie, metallic foil tape wound over the bougie, or a metallic material embedded in the rod, i.e., a wire or flattened wire).

Tracheal tubes have an inherent arcuate shape, and a standard bougie cannot keep it in a straightened position. Conversely, this is exactly what a stylet does—allowing straightening of the main body of the tube (and upturning the distal tip). The two malleable sections 504 and 508 enable introducer 500 to retain a bendable shape at two points. This permits a variety of shaping options, either with or without an overlying tracheal tube.

By having two malleable sections 504 and 508 with greater rigidity than the intervening distal section 506, there is a preferential movement and flexibility between the malleable sections. For example, when a tracheal tube is slid over introducer 500 configured for use as a stylet, the malleable sections 504 and 508 can be shaped with the shape being maintained for tube insertion, but, upon insertion further into the trachea, the distal section 506 between the two malleable sections allows introducer 500 to unbend.

Figure 5D:
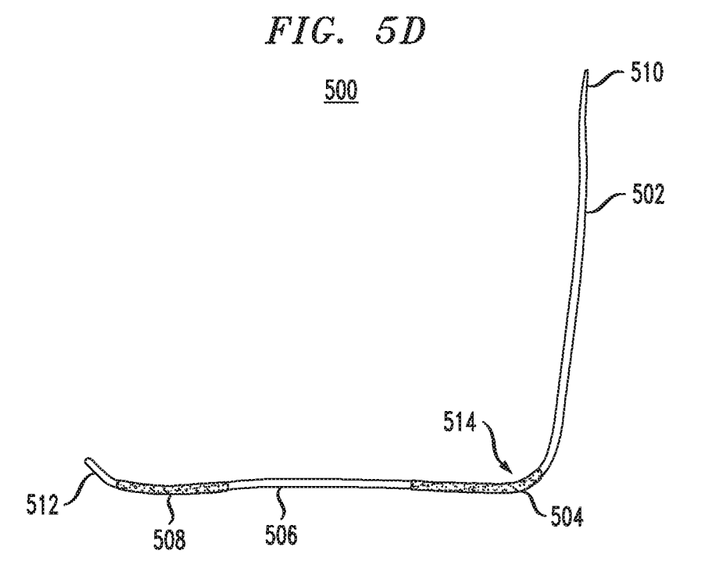
FIG. 5D shows the introducer of FIG. 5A configured for use as a bougie.

FIG. 5D shows introducer 500 configured for use as a bougie with the first malleable section 504 bent by about 90 degrees to form a grip region 514 for an operator, where proximal section 502 is roughly co-planar with bougie tip 512. After insertion of the bougie tip 512 into the trachea, the operator can straighten the bent malleable section 504 (for example, with one hand) and railroad a tracheal tube over the introducer's back end and into the trachea (for example, using the operator's free hand).

Figure 5E:
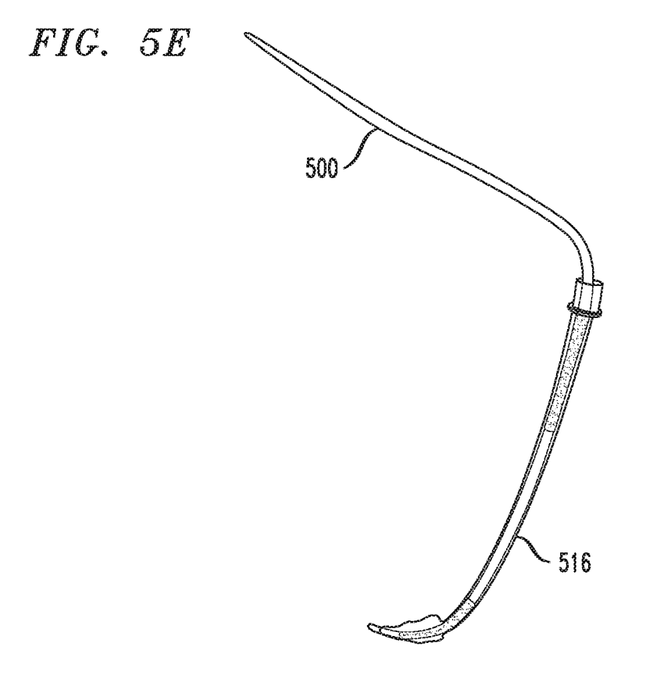
FIG. 5E shows the introducer of FIG. 5D pre-loaded with a tracheal tube.

FIG. 5E shows introducer 500 having the configuration of FIG. 5D but pre-loaded with a tracheal tube 516. With the tracheal tube 516 inserted up to the 90-degree bend, an operator can grip with one hand both the proximal end of the tube and the introducer at the bend for efficient insertion of the styletted tube into the trachea.

Figure 5F:
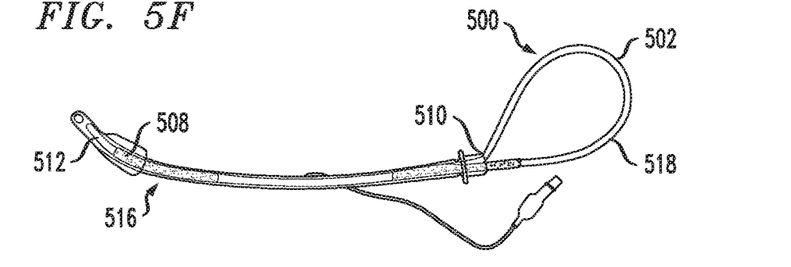
FIG. 5F shows a side view of the introducer of FIG. 5A configured for use as a stylet for direct laryngoscopy with a pre-loaded tracheal tube.
Figure 5G:
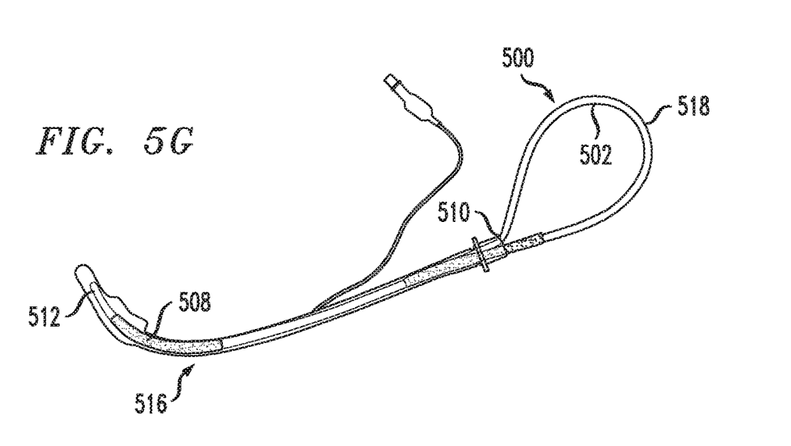
FIG. 5G shows a side view of the introducer of FIG. 5A configured for use as a stylet for video laryngoscopy with a pre-loaded tracheal tube.
Figure 5H:
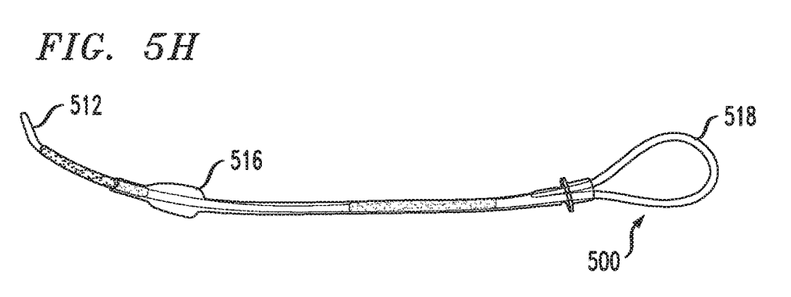
FIG. 5H shows a side view of the introducer of FIG. 5A configured for use as a stylet.

FIG. 5F shows a side view of introducer 500 configured for use as a stylet for direct laryngoscopy (i.e., with an about 35-degree bend at its second malleable section 508) with a pre-loaded tracheal tube 516, while FIG. 5G shows a side view of introducer 500 configured for use as a stylet for video laryngoscopy (i.e., with an about 70-degree bend at its second malleable section 508) with pre-loaded tracheal tube 516. In these configurations, a handle 518 is formed by bending the flexible proximal section 502 by a total of about 180 degrees and forcing the flattened proximal tip 510 into the proximal end of the overriding tracheal tube 516 to secure everything in place. Note that the length at which introducer 500 is inserted within tube 516 determines (i) whether the distal end of tube 516 extends beyond the distal tip 512 of introducer 500, or vice versa, and (ii) the size of handle 518. FIG. 5H shows a side view of introducer 500 configured for use as a stylet in which (i) the distal tip 512 of introducer 500 extends beyond the distal end of tube 516 and (ii) handle 518 is smaller than the handles of FIGS. 5F and 5G.

The flattened proximal tip 510 gives introducer 500 an inherent directionality (i.e., the operator knows the orientation of the distal introducer tip 512 by the orientation of the flattened proximal tip 510). By curling the proximal section 502 over itself (and securing it through the tracheal tube connector), the introducer's length is shortened which makes it easier to handle and insert into the trachea. The proximal curl provides an ergonomically effective way to control the introducer and also gives the operator an indication of the orientation of the upturned bougie tip 512.

Figure 5I:
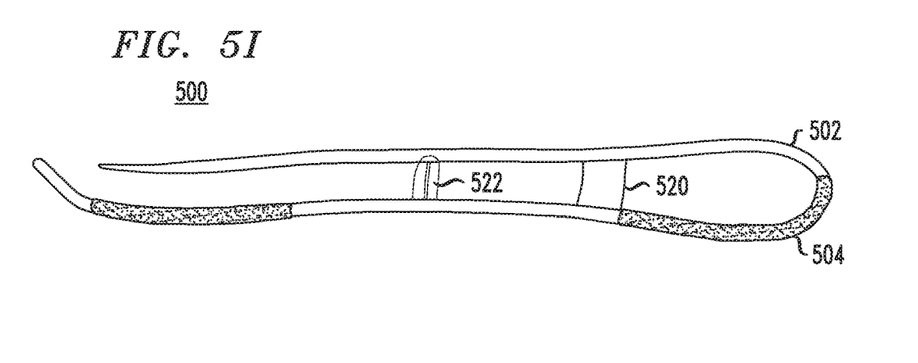
FIG. 5I shows a side view of the introducer of FIG. 5A configured for efficient packaging or storage.

FIG. 5I shows a side view of introducer 500 configured for efficient packaging or storage with the flexible proximal section 502 and the first malleable section 504 providing a total bend angle of about 180 degrees. Note that tape 520 or other fixture 522 may be employed to secure introducer 500 in this configuration.

The standard approach to dealing with a hyperangulated stylet is to withdraw the stylet after the tube tip is through the cords, and then try pushing the tube down into the trachea. But the tube comes off the stylet pointing upward, following the upward arc of the stylet, not the downward inclination of the trachea. This can cause mechanical impaction. In another approach, the stylet and tube are both turned rightward 90 degrees. The tube can then be advanced off the stylet with one hand (i.e., can be done without assistance). In another approach, the tube alone is rotated rightward 90 degrees (e.g., with assistance from another person). Both approach solve the problems of corrugation (bevel up) and inclination (tube down).

The introducer 500 is a tube introducer with a narrow, long axis and an upturned distal tip 512. The introducer 500 has an outer diameter small enough (e.g., 5 mm) to receive any tracheal tube. The upturned tip facilitates visualization and bounces off the trachea rings, providing a tactile confirmation of tracheal placement. It is useful to know the direction of the upturned tip on placement, especially in poor views. The grips shown in FIGS. 5E-5H labelled above allow this (unlike a standard pencil grip on device).

Unless explicitly stated otherwise, each numerical value and range should be interpreted as being approximate as if the word "about" or "approximately" preceded the value or range.

It will be further understood that various changes in the details, materials, and arrangements of the parts which have been described and illustrated in order to explain embodiments of this invention may be made by those skilled in the art without departing from embodiments of the invention encompassed by the following claims.

In this specification including any claims, the term "each" may be used to refer to one or more specified characteristics of a plurality of previously recited elements or steps. When used with the open-ended term "comprising," the recitation of the term "each" does not exclude additional, unrecited elements or steps. Thus, it will be understood that an apparatus may have additional, unrecited elements and a method may have additional, unrecited steps, where the additional, unrecited elements or steps do not have the one or more specified characteristics.

The use of figure numbers and/or figure reference labels in the claims is intended to identify one or more possible embodiments of the claimed subject matter in order to facilitate the interpretation of the claims. Such use is not to be construed as necessarily limiting the scope of those claims to the embodiments shown in the corresponding figures.

Reference herein to "one embodiment" or "an embodiment" means that a particular feature, structure, or characteristic described in connection with the embodiment can be included in at least one embodiment of the invention. The appearances of the phrase "in one embodiment" in various places in the specification are not necessarily all referring to the same embodiment, nor are separate or alternative embodiments necessarily mutually exclusive of other embodiments. The same applies to the term "implementation."

What is claimed is:

1. An introducer for tracheal tube intubation, the introducer comprising a proximal section connected by an intermediate section to a distal section having an angled bougie tip, wherein:

the introducer can be configured for use as a bougie in which a tracheal tube is railroaded over a back end of the introducer and into a trachea;

the introducer can be configured for use as a stylet in which a tracheal tube is pre-loaded onto the introducer for insertion into a trachea; and the intermediate section comprises an attachment mechanism that secures the proximal section to the intermediate section when the proximal section is bent to form a handle.

2. The introducer of claim 1, wherein the attachment mechanism comprises a recess that receives the proximal section when the proximal section is bent to form the handle.

3. The introducer of claim 2, wherein the proximal section is substantially parallel to the intermediate section when the recess receives the proximal section to form the handle.

4. The introducer of claim 1, wherein the attachment mechanism comprises an opening that receives the proximal section when the opening receives the proximal section to form the handle.

5. The introducer of claim 4, wherein the attachment mechanism further comprises a protrusion from the opening that holds the proximal section in place when the proximal section is bent to form the handle.

6. The introducer of claim 4, wherein the proximal section is substantially orthogonal to the intermediate section when the opening receives the proximal section to form the handle.

7. The introducer of claim 1, wherein the attachment mechanism comprises a clip that wraps around the intersecting intermediate and proximal sections when the proximal section is bent to form the handle.

8. The introducer of claim 7, wherein the clip is relocatable to different positions along the intermediate section to form handles of different size.

9. The introducer of claim 7, wherein the proximal section is substantially orthogonal to the intermediate section when the clip wraps around the intersecting intermediate and proximal sections to form the handle.

10. The introducer of claim 1, wherein the attachment mechanism comprises a component of a male-female assembly, wherein a male component of the assembly engages a female component of the assembly when the proximal section is bent to form the handle.

11. The introducer of claim 10, wherein the male component is part of the proximal section and the female component is part of the intermediate section.

12. The introducer of claim 11, wherein:
the intermediate section comprises at least first and second female components;
when the proximal section is bent such that the male component engages the first female component, the proximal section is bent to form a relatively large handle; and
when the proximal section is bent such that the male component engages the second female component, the proximal section is bent to form a relatively small handle.

13. The introducer of claim 10, wherein the proximal section is substantially orthogonal to the intermediate section when the male component engages the female component to form the handle.

14. The introducer of claim 10, wherein:
the male component comprises a cap connected to a center post having a diameter smaller than the diameter of the cap; and
the female component comprises two posts separated by more than the diameter of the male component's center post and less than the diameter of the male component's cap such that the female component holds the male component in place between the female component's two posts when the male component engages the female component to form the handle.

15. The introducer of claim 1, wherein the proximal section is malleable.

16. The introducer of claim 15, wherein the intermediate section is flexible.

* * * * *